(12) United States Patent
Zakaria et al.

(10) Patent No.: US 8,920,428 B2
(45) Date of Patent: Dec. 30, 2014

(54) SURGICAL INSTRUMENTATION SPECIFIC TO A PATIENT FOR PREPARING A BONE OF THE PATIENT

(71) Applicant: Tornier SAS, Montbonnot-Saint-Martin (FR)

(72) Inventors: Toufik Zakaria, Grenoble (FR); Emmanuel Lizee, Saint Ismier (FR)

(73) Assignee: Tornier, Montbonnot Saint Martin (FR)

( * ) Notice: Subject to any disclaimer, the term of this patent is extended or adjusted under 35 U.S.C. 154(b) by 137 days.

(21) Appl. No.: 13/677,976

(22) Filed: Nov. 15, 2012

(65) Prior Publication Data

US 2013/0197528 A1    Aug. 1, 2013

Related U.S. Application Data

(60) Provisional application No. 61/560,903, filed on Nov. 17, 2011.

(30) Foreign Application Priority Data

Nov. 15, 2011 (FR) ...................................... 11 60368

(51) Int. Cl.
*A61B 17/60* (2006.01)
*A61B 17/58* (2006.01)
*A61F 2/00* (2006.01)
*A61B 17/15* (2006.01)
*A61B 17/56* (2006.01)

(52) U.S. Cl.
CPC ......... *A61B 17/155* (2013.01); *A61B 2017/568* (2013.01)
USPC ......................................... 606/88

(58) Field of Classification Search
USPC ........................................... 606/88
See application file for complete search history.

(56) References Cited

U.S. PATENT DOCUMENTS

| 8,668,700 | B2* | 3/2014 | Catanzarite et al. ............ 606/88 |
| 2008/0161815 | A1 | 7/2008 | Schoenefeld et al. |
| 2009/0087276 | A1 | 4/2009 | Rose |
| 2010/0087829 | A1 | 4/2010 | Metzger et al. |
| 2011/0071533 | A1 | 3/2011 | Metzger et al. |

OTHER PUBLICATIONS

French Search Report issued in French Application No. 1160368, dated Jan. 31, 2012, one page.

* cited by examiner

*Primary Examiner* — Sameh Boles
(74) *Attorney, Agent, or Firm* — Knobbe Martens Olson & Bear LLP

(57) ABSTRACT

Embodiments of the present invention relate to surgical instrumentation specific to a patient for preparing a bone including a patient-specific block delimiting a supporting surface shaped to fit the bone, and a main portion partly delimiting the fixed supporting surface and at least two primary orifices for receiving a primary pin, crossing the block between the supporting surface and an opposite surface. The instrumentation also includes a secondary portion which belongs to the block, partly delimits the supporting surface and includes at least two secondary orifices for receiving a bone preparation tool crossing the block between the supporting surface and opposite surface, and a mechanism for mechanically disengaging the secondary portion with respect to the main portion, suitable for, when the main portion is attached onto the bone with primary pins passed into the primary orifices, making the secondary portion removable with respect to the main portion.

15 Claims, 11 Drawing Sheets

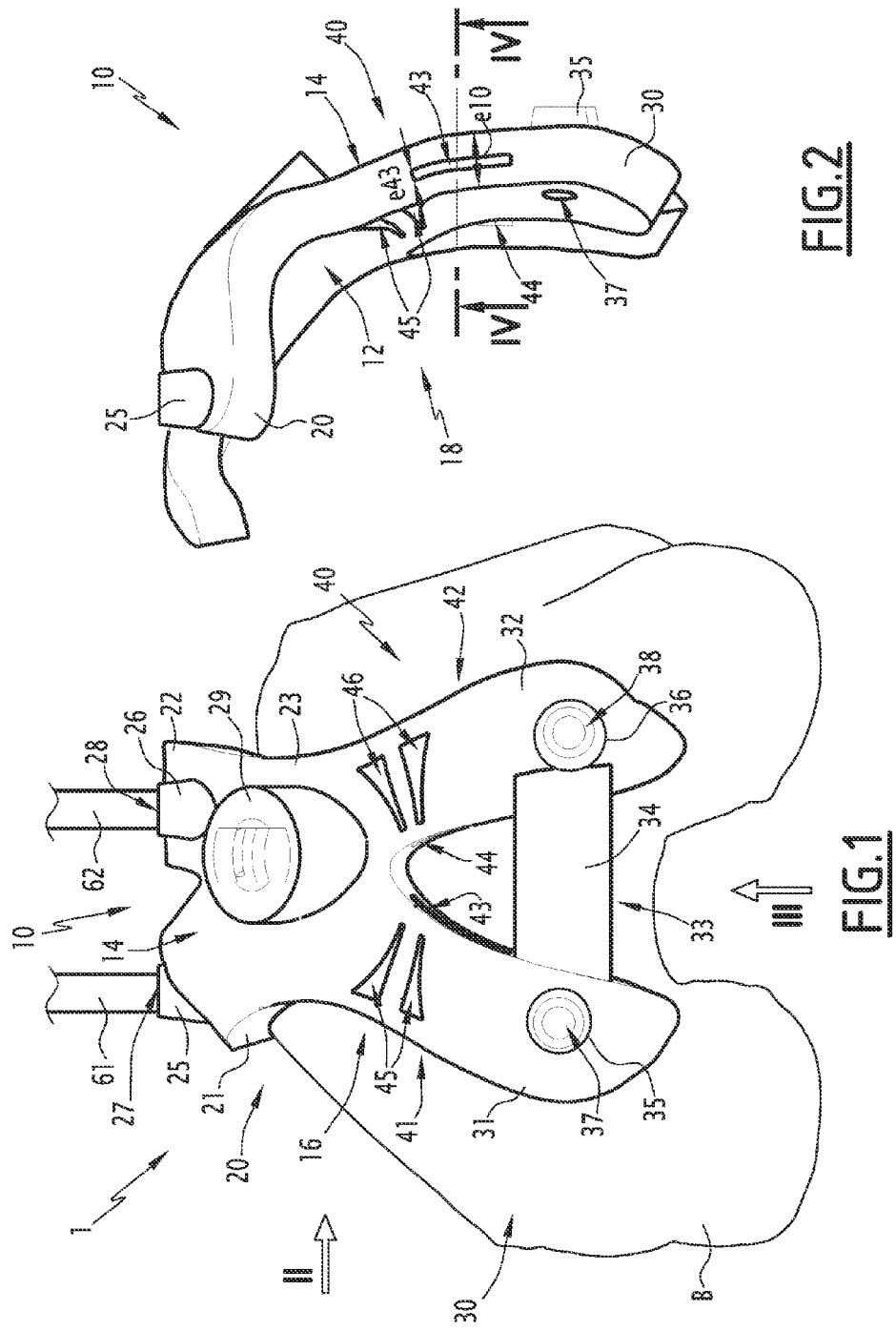

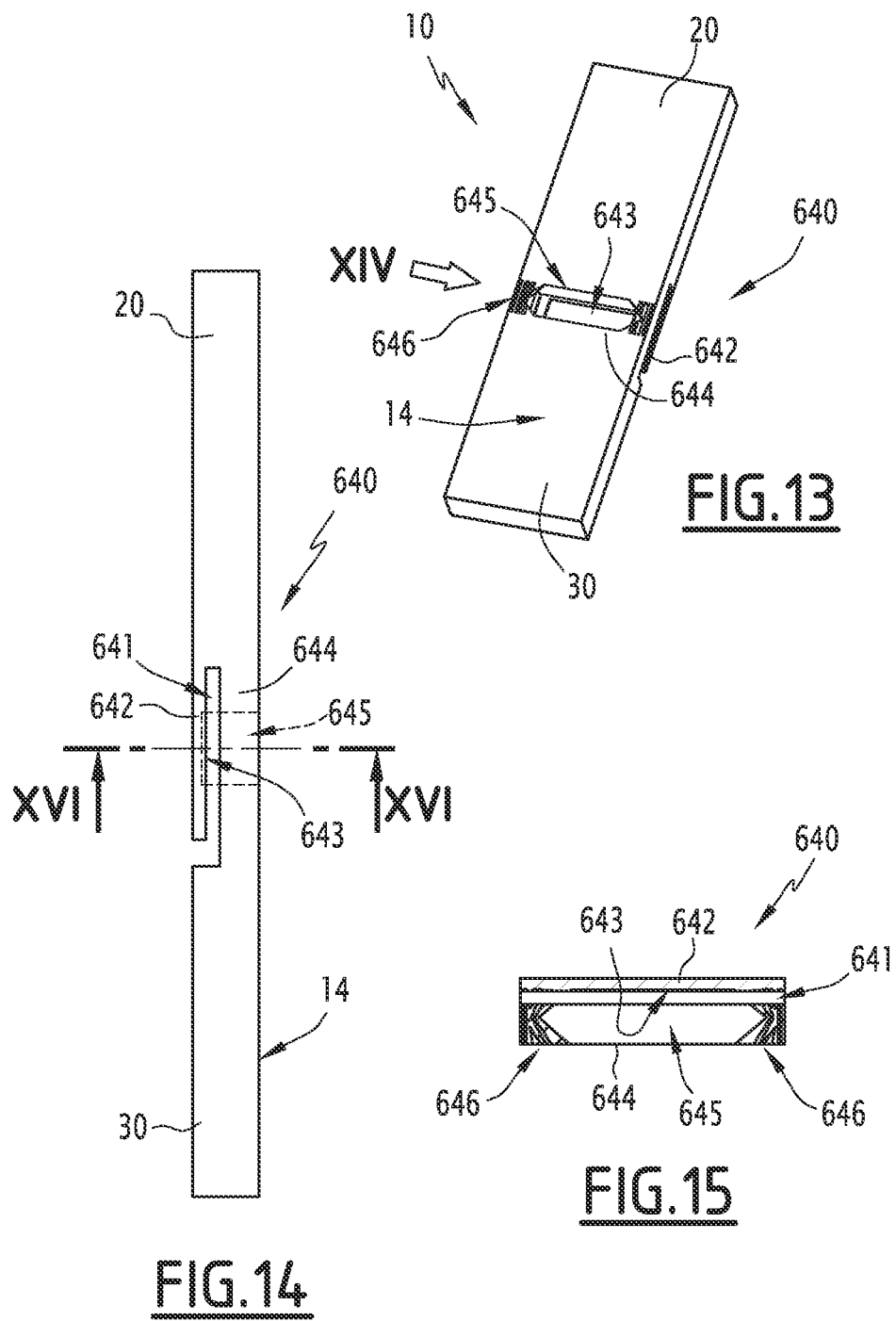

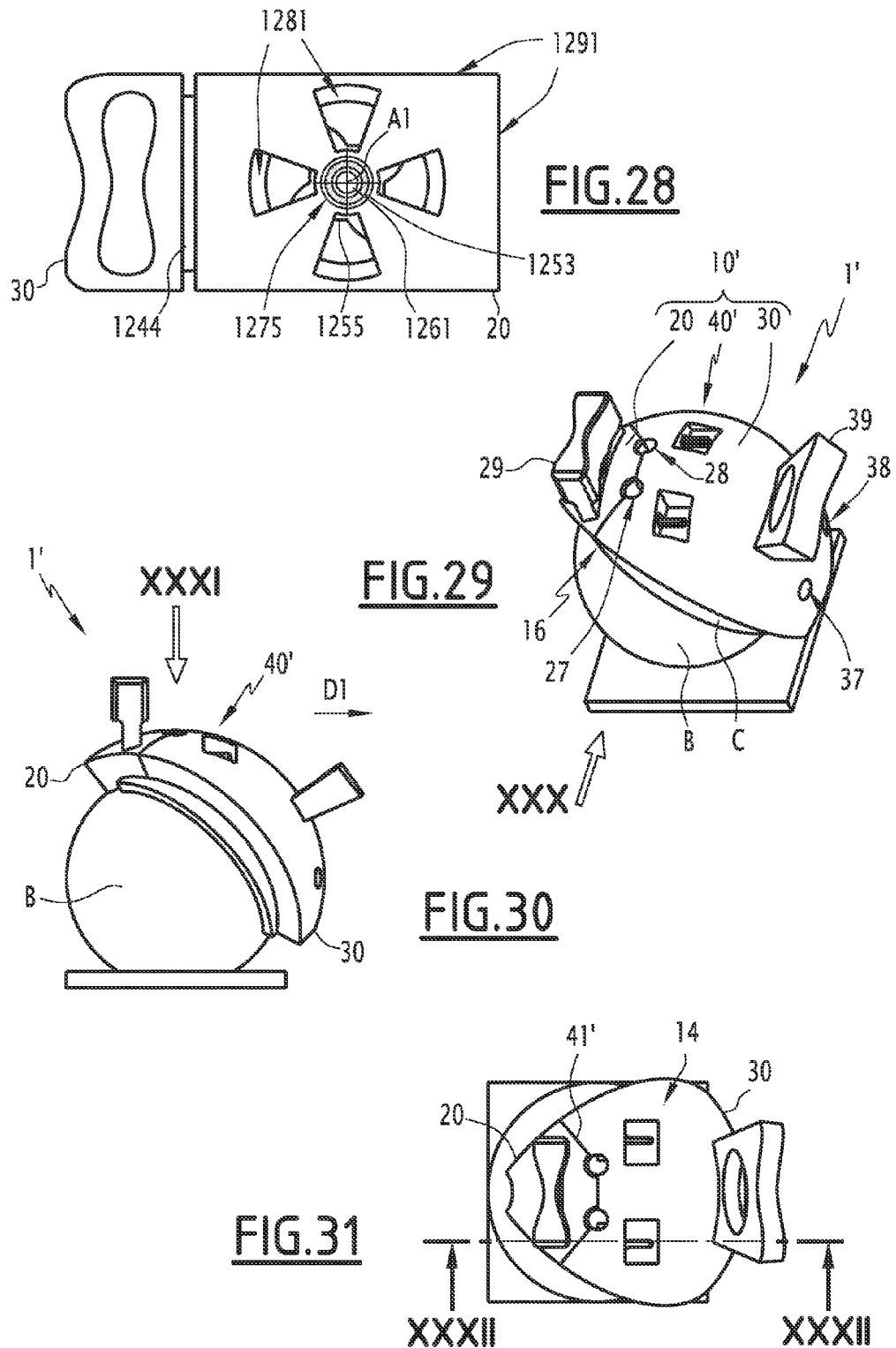

SURGICAL INSTRUMENTATION SPECIFIC TO A PATIENT FOR PREPARING A BONE OF THE PATIENT

CROSS-REFERENCE TO RELATED APPLICATION

This application claims the benefit of U.S. Provisional Patent Application Ser. No. 61/560,903, filed on Nov. 17, 2011, and claims foreign priority to French Patent Application No. 1160368, filed on Nov. 15, 2011, both of which are incorporated herein by reference in their entireties for all purposes.

TECHNICAL FIELD

Embodiments of the present invention relate to surgical instrumentation specific to a patient, for preparing a bone of the patient, for example a femur, for implanting a prosthesis component therein.

The field of the invention relates to tailored or customized instrumentation, in connection with a specific patient, on which the instrumentation is intended to be used by a surgeon. This kind of patient-specific instrumentation is in contrast to standard instrumentations which are also used on different patients, if necessary by being reused several times successively, while being cleaned and sterilized between each use.

BACKGROUND

The advent of tailored surgical instrumentation is related to present possibilities of acquiring sufficiently accurate pre-operative data in order to design from a dimensional point of view, instruments for which the interfaces for mechanical cooperation with the bones of the patient are specifically defined by taking into account the specific shape, notably the surface reliefs of these bones. The pre-operative data used typically stem from scanner images or more generally from any recording of bone mapping data advantageously obtained in a non-invasive way. These data are processed by a computer in order to control the manufacturing of tailored surgical instruments, once the surgeon has decided on the details of the surgical procedure which the surgeon will follow during a future operation.

During the operation, the surgeon positions on the bone a guiding block, including a shaped surface so as to specifically fit the bone of the patient. The guiding block then allows guidance of the application on the bone of a bone preparation tool, such as a boring bit or an anchoring pin. Subsequently, the guiding block has to be removed or moved away from the bone so as to allow the positioning of a cutting block. As the shape of the guiding block fitting the bone is relatively complex, this makes it difficult, or even impossible to remove the bone when the pins are inserted therein.

SUMMARY

Embodiments of the present invention improve surgical instrumentation, providing the surgeon with a gain in time and in accuracy. Embodiments of the invention include patient-specific surgical instrumentation for preparing a bone of the patient, the instrumentation comprising a block specific to the patient delimiting a fixed supporting surface on the bone, which is shaped so as to be specifically fitted to this bone, and including a main portion which partly delimits the fixed supporting surface and which delimits at least two primary orifices for respectively letting through a primary pin, these primary orifices crossing the block between the supporting surface and an opposite surface of the block, the instrumentation also including a secondary portion which belongs to the block, which partly delimits the supporting surface and which includes at least two secondary orifices for respectively letting through a bone preparation tool, such as a boring bit or an anchoring pin, these secondary orifices crossing the block between the supporting surface and the opposite surface of the block, and a mechanism for mechanically disengaging the secondary portion with respect to the main portion, suitable for, while the main portion is attached on the bone by primary pins having passed into the primary orifices, making the secondary portion removable with respect to the main portion.

The mechanical disengagement mechanism may comprise at least one patient-specific cavity, which extends through the block, between the main portion and the secondary portion, along a geometrical envelope of the fixed supporting surface.

Thus, embodiments of the invention facilitate per-operative manipulations of the surgeon. The instrumentation is simple and practical to use: the specific block is suitable for positioning on the bone, secondary pins which will be subsequently used for placing on the bone a cutting block or any other system for preparing the bone on the one hand, and then for being entirely or partly disengaged from the bone without altering the accuracy of the positioning of these pins on the other hand. The surgeon simply has to break, cut, fold, unclip or remove the mechanism for mechanical disengagement of the secondary portion with respect to the main portion, depending on the embodiment of this mechanism. In order to avoid a loss of accuracy resulting from the disassembling and reassembling of pins, the surgeon may guide the application of a boring bit or the like by the secondary portion, before placing the secondary pins in the pierced holes in the bone after disengagement of the secondary portion, or to leave the secondary pins in place in the bone during the at least partial removal of the guiding block. In practice, the disengagement of the secondary portion is achieved along a direction which does not induce any jamming interference between the portion of the supporting surface, delimited by this secondary portion, and the release of the femur to which is fitted this portion of the supporting surface.

Embodiments of the invention permit the possibility of forming areas with reduced mechanical strength, more easily deformable and/or sectile, while ensuring that the block has sufficient mechanical strength during its positioning on the bone and during the insertion of the pins. With a cavity non-specific to the patient, in other words a generic cavity, such a compromise would be difficult to obtain because of the complex geometry of the bone. From one patient to another, instrumentation comprising a generic cavity would not be satisfactory. On the other hand, with the patient-specific cavity or cavities, the instrumentation according to embodiments of the invention facilitates per-operative manipulations of the surgeon.

Some embodiments of the present invention include one or a combination of the following features and/or characteristics:

The block and the specific cavity each have a substantially constant thickness, along a direction normal to the fixed supporting surface, at the mechanical disengagement mechanism.

The block includes at least one vent opening into the specific cavity on the one hand and at the fixed supporting surface or at the opposite surface of the block, on the other hand.

The mechanical disengagement mechanism comprises two patient-specific cavities, which extend through the block along a geometrical envelope of the fixed supporting surface.

Said or each specific cavity includes at least one aperture opening outside the block.

The mechanical disengagement mechanism is further suitable for, when the secondary pins are passed into the secondary orifices, making the secondary portion removable with respect to the main portion by sliding along the secondary pins.

The mechanical disengagement mechanism is made both with the main portion and the secondary portion of the same material.

The mechanical disengagement mechanism is made both with the main portion and the secondary portion of the same material during the manufacturing of the block by laser powder sintering.

The mechanical disengagement mechanism comprises at least one connecting element which connects the main portion and the secondary portion and which may be destroyed by breaking, tearing off and/or by severance.

The mechanical disengagement mechanism comprises at least one aperture for receiving a tool in contact with the connecting element(s) for the breaking, tearing off and/or severance of the connecting element(s).

The block and the specific cavity each have a substantially constant thickness, along a direction normal to the fixed supporting surface, at the mechanical disengagement mechanism.

The mechanical disengagement mechanism comprises an elastically deformable element which connects the main portion and the secondary portion and allows reversible disengagement by folding the secondary portion with respect to the main portion.

The mechanical disengagement mechanism comprises a rotary member and in that a rotation of the rotary member exerts forces on the connecting element(s) for breaking, tearing off and/or severing the connecting element(s).

The mechanical disengagement mechanism is suitable for successively being secured to the block and then at least partly detached from the block, notably by clipping/unclipping or by screwing/unscrewing.

The mechanical disengagement mechanism is at least partly made in the same material, with a first portion from among the main portion and the secondary portion.

The mechanical disengagement mechanism includes at least one element for temporary adhesion of the first portion onto a second portion from among the main portion and the secondary portion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is an elevational view of instrumentation according to an embodiment of the present invention, including a specific block fitted on a left femur of a patient, the observation direction of this FIG. 1 corresponding to the longitudinal direction of the femur.

FIG. 2 is a perspective view of the specific block, slightly from the rear and without the femur, along the arrow II in FIG. 1.

FIG. 13 is a partial perspective view of instrumentation according to a seventh embodiment of the invention.

FIG. 14 is an elevational view along the arrow XIV in FIG. 13.

FIG. 15 is a sectional view along the line XV-XV in FIG. 12.

FIG. 28 is a sectional view in the plane XXVIII in FIG. 25.

FIG. 29 is a perspective view of instrumentation according to another embodiment of the invention, comprising a specific block fitted onto a femur schematically shown;

FIG. 30 is an elevational view along the arrow XXX in FIG. 29, the observation direction of this FIG. 30 corresponding to the latero-medial direction of the femur.

FIG. 31 is an elevational view along the arrow XXXI in FIG. 30.

Figure 3:
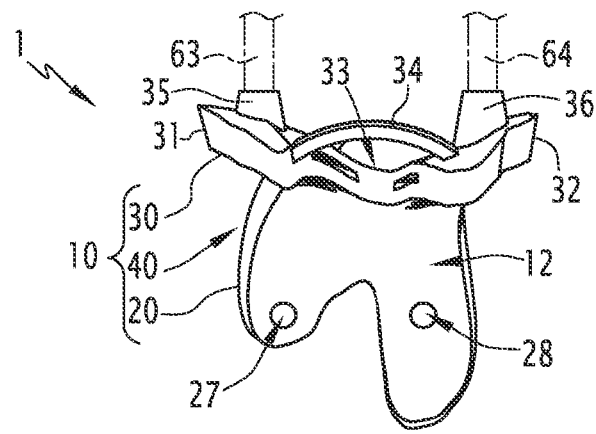
FIG. 3 is an elevational view along the arrow III in FIG. 1, the femur not being shown.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In FIGS. 1 to 5, is illustrated surgical instrumentation 1 specific to a patient, for preparing a bone B of this patient with view to implanting a prosthesis.

More specifically, in the example of FIGS. 1 to 5, the bone is the right femur of the patient, to be prepared for implanting a prosthesis femoral component of the knee. It is understood that the specific surgical instrumentation 1 according to the invention may be suitable for different bones of the human or animal body.

In all the following, the terms of "upper", "lower", "posterior" and the like are meant in their usual anatomical meaning, while considering that the operated patient is standing on a horizontal surface.

Prior to the surgical implantation operation, mapping data relating the femur B of the patient are collected. In practice, these pre-operative mapping data may be obtained in various ways. As an example, scanner and/or X-ray images and/or ultrasonographies, and/or MRIs of the femur B are used. In all cases, at the end of this preliminary data acquisition step, a sufficient amount of information is available for designing and making a patient-specific femoral block 10. The block 10 is shown in position on the femur B in FIG. 1 and alone in FIGS. 2 to 5.

The specific femoral block 10 has a surface 12 intended to be turned towards the femur B, and a surface 14 intended to be turned towards the surgeon when the block 10 is fitted on the femur B. The surface 12 is shaped so as to be specifically fitted to the lower end of the femur B and, when operating, is fixedly pressed against this end of the femur B, by fitting the surface of the latter by shape mating. It is understood that in order to end up with such a strict fit between the supporting surface 12 and the lower end of the femur B, the surface 12 is drawn by using the pre-operative mapping data relating to the femur. In this way, the supporting surface 12 has customized reliefs which are specific to the patient which, by cooperating with mating reliefs delimited by the surface of the lower end of the femur, only allow a single supporting configuration fitted on the femur B, as illustrated in FIG. 1. As an example, in FIG. 1, the supporting surface 12 covers anterior and distal areas of the lower end of the femur B, by closely fitting the reliefs of these areas.

When operating, the specific femoral block 10 may be fixedly pressed through its surface 12 onto the lower end of the femur B. This attachment may be achieved by two through-holes 27 and 28 made through two guiding studs, 25 and 26 respectively, these holes 27 and 28 connecting the surface 12 with the surface 14 opposite to the block 10 on the one hand and two bone anchoring pins 61 and 62 able to be respectively engaged in a mating way into the through-holes 27 and 28, as illustrated in FIG. 1, until they are stuck and thus immobilized in the bone material of the femur B.

At this stage, it is noted that the specific femoral block 10 includes two portions having different respective purposes, as explained below, i.e. a main portion 20, as well as a secondary portion 30 which is detachable from the main portion 20. A junction area 16 connects the portions 20 and 30 of the specific femoral block 10, which appears as an initially monolithic shape. The block 10 may be made in any known way, suitable for the present application. The block 10 may be made by selective laser powder sintering. In this case, the solidified block 10 is surrounded with residual powder after its fabrication, and then the powder is first removed by sweeping and then by blowing, the block 10 may then be removed from the manufacturing container, cleaned and then sterilized before being used on a patient.

As shown in FIG. 1, the main portion 20 includes two branches 21 and 22 which extend from a central portion 23. The studs 25 and 26 are formed on the surface 14 of the block 10, on the branches 21 and 22 respectively. In other words, the branch 21 is crossed by the hole 27, while the branch 22 is crossed by the hole 28. The central portion 23 is provided, protruding from the surface 14, with a stud 29 for attaching a cutting block or any other system for preparing the femur B, not shown, during a subsequent per-operative step. The central portion 23 delimits by itself the major portion of the material of the block 10 and of the supporting surface 12.

In the embodiments of FIGS. 1 to 5, the secondary portion 30 includes two branches 31 and 32 which extend from the central portion 23 at the junction area 16 in the extension of the branches 21 and 22 respectively, while following the surface of the femur B. The elements 21, 22, 23, 31 and 32 delimit together the supporting surface 12. Studs 35 and 36 are formed on the surface 14 of the block 10, respectively on the branches 31 and 32. The secondary portion 30 is provided with two through-holes 37 and 38 made in the guiding studs, 35 and 36, respectively, which are each provided for receiving a bone preparation tool, such as a boring bit or a bone anchoring pin: in FIG. 3, such bone preparation tools referenced as 63 and 64, respectively, are shown in dotted lines. The branches 31 and 32 are separated by an intermediate space 33, intended to be placed during operation in the extension of the intercondylar space, as shown in FIG. 1. A plate 34 extends through the space 33 while connecting the branches 31 and 32, for example in order to stiffen the secondary portion 30. This plate 34 does not define the supporting surface 12 and is therefore, during operation, distant from the surface of the femur B. Thus, the plate 34 does not enter the intercondylar space and does not conceal it entirely. Alternatively, the plate 34 may include inscriptions useful for the surgeon, or the block 10 does not include any plate 34.

When operating, the main portion 20 is present during the whole use of the instrumentation 1, in the sense that this main portion 20 is both the first to be placed, while being attached to the femur B by the pins 61 and 62 which may thus be described as primary pins, and the last disengaged with respect to the femur, while the secondary portion 30 is on the contrary separated from the main portion 20, during use, by the surgeon. Insofar that the specific femoral block 10 is made available to the surgeon in an initially monolithic shape, the separation of the secondary portion 30 relative to the main portion 20 requires that the surgeon break the material connection between the portions 20 and 30, at the junction area 16. In fact, the temporary presence, during the operation, of the secondary portion 30 relative to the remainder of the block 10 gives the possibility of properly understanding the benefit of the present invention.

Indeed, the secondary portion 30 corresponds to the portion of the block 10 which was designed, in a pre-operative way, for guiding the per-operative application on the femur B of the preparation tools 63 and 64, such as a boring bit or an anchoring pin, via the holes 37 and 38. In the detail of surgical practice, it is understood that two operating approaches are possible with respect to the holes 37 and 38: First, either these holes 37 and 38 are used for guiding the application of a boring bit or of a similar tool, which is disengaged as soon as its boring action on the femur is completed; in this case in a subsequent step of the surgery, the blind holes which have thus been bored into the femur are used for receiving secondary anchoring pins, the purpose of which is described below. Or, second, these holes 37 and 38 are used for guiding the application of anchoring pins or the like, these pins being optionally placed after a pre-hole has been made in the femur by a boring tool introduced through the holes 37 and 38; in this case, once these anchoring pins are set into place via the holes 37 and 38, they may remain in place until the aforementioned subsequent step and thereby form secondary anchoring pins, similar to those described just above.

During the tailored design of the block 10, the holes 37 and 38 are positioned within the block 10 so as to accurately orientate the aforementioned secondary pins: during surgery, during the aforementioned subsequent step, these secondary pins are used for guiding in turn the positioning of the mechanism for cutting the femur B, such as a cutting block, in order to resect the end of the femur B along one or several dimensioned resection planes for subsequently forming corresponding planar supports for attachment of a femoral prosthetic component. Thus, the disengagement of the secondary portion 30 frees space facing the area of the femur B into which the holes 37 and 38 opened until then, i.e. the distal area of the lower end of the femur B.

For this purpose, the instrumentation 1 includes a mechanism 40 for mechanical disengagement of the secondary portion 30 with respect to the main portion 20 and to the femur B, this mechanism 40 being positioned in the junction area 16 and the main portion 20 and the secondary portion 30. In the example of FIGS. 1 to 5, the mechanical disengagement mechanism 40 is made both with the main portion 20 and the secondary portion 30 in the same material, notably during the making of the block 10 by laser powder sintering.

Figure 4:
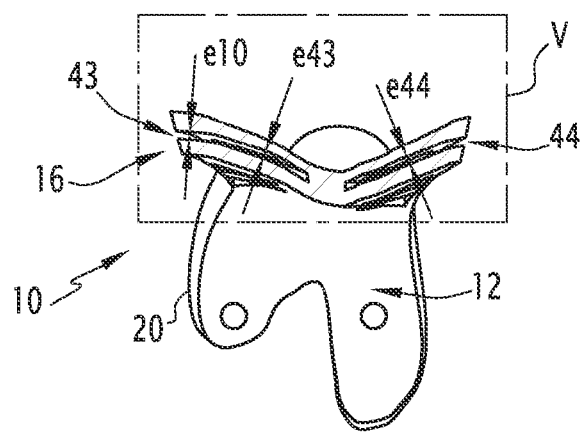
FIG. 4 is a sectional view along the line IV-IV in FIG. 2.
Figure 5:
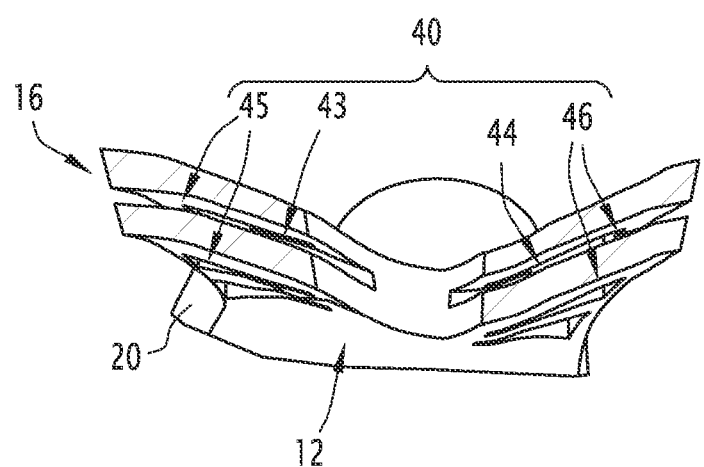
FIG. 5 is a view at a larger scale of the detail V in FIG. 4.

Given the arrangement of the branches 31 and 32 with the central portion 23, the mechanism 40 is distributed between a first region 41 located between the branch 31 and the portion 23 and a second region 42 located between the branch 32 and the portion 23. In each region 41 and 42, the mechanism 40 includes a cavity 43 and 44 respectively. Each cavity 43 and 44 crosses the block 10 in the junction area 16 and opens on either side of the branches 31 and 32, at the space 33 and opposite to the space 33, i.e. globally along the latero-medial direction during operation. Each cavity 43 and 44 is said to be enveloping, insofar that it extends through the block 10 by fitting the outer shape of the femur B, in other words along the geometry of the surface 12 and may therefore be described as a patient-specific cavity, corresponding to the patient's particular morphology. As shown in FIGS. 2 and 4, the block 10 has a thickness e10, measured between the surface 12 and the surface 14 in a direction normal to the surface 12, which is substantially constant in the junction area 16 where the mechanism 40 is located. Further, each cavity 43 and 44 has a thickness, e43 and e44 respectively, which is constant in the direction normal to the surface 12.

As shown in FIG. 1, the mechanism 40 also includes vents 45 and 46, made through the block 10, in the region 41 and the region 42, respectively. The vents 45 open into the cavity 43, with two vents 45 which open at the surface 12 and two vents which open at the surface 14. Also, the vents 46 open into the cavity 44, with two vents 46 which open at the surface 12 and two vents 46 which open at the surface 14. The vents 45 and 46 have a suitable profile for facilitating deformation of the material in each of the regions 41 and 42. In the non-limiting example of FIGS. 1 to 5, the vents 45 and 46 have the shape of an irregular quadrilateral, notably with a planar face and a face with a substantially hyperbolic curved shape placed opposite, which extend along the direction normal to the surface 12.

When the block 10 is made by powder sintering, the cavities 43 and 44 open out of the block 10, on the sides of the branches 31 and 32 and at the vents 45 and 46 which allows the powder to be evacuated. In the opposite case, the powder trapped in the cavities would risk being poured on the bone of the patient. In other words, within the scope of the invention, the cavities 43 and 44 include at least one aperture opening out of the block 10.

In practice, the mechanical disengagement of the secondary portion 30 with respect to the main portion 20 and to the femur, on which this main portion 20 is attached by the primary pins 61 and 62, is achieved by breaking the material of the block 10 at the mechanism 40. The regions 41 and 42 may be folded and torn off when the portion 30 is moved away from the femur B, with the orifices 37 and 38. Indeed, the cavities 43 and 44 and the vents 45 and 46 form breaking points facilitating the separation of the portions 20 and 30. In other words, the mechanism 40 forms localized weakening elements of the material of the block 10 in the area 16. Mechanical disengagement may be carried out manually or preferably by means of a tool, notably of the osteotome, screwdriver or retractor type. Optionally, this disengagement tool may be shaped so as to be able to be housed at the same time in the vents 45 and 46, so that an action of the surgeon on the tool may tear off or deform the material of the regions 41 and 42 simultaneously.

Due to the mechanism 40 being directly integrated to the block 10, this block 10 is able to be disengaged from the femur B, at the secondary portions 30, with the pins 61 and 62 which are in place in the block 10 and the femur B. As described above, this disengagement of the secondary portion 30 may be either achieved while the holes 37 and 38 are clear, after having guided a boring bit or the like, or while secondary pins have passed into these holes and remain in place in the femur until the subsequent operating step inclusively, as explained above. In the second case, it will be noted that the disengagement of the secondary portion 30 is accompanied by the sliding of this portion 30 along the aforementioned secondary pin. Of course, in the first case, the disengagement of the secondary portion 30 may be carried out in other directions, by moving away from the femur B; however, the separation of the secondary portion 30 with respect to the main portion 20 may involve the possibility of being able to move the portion 30 away in a non-blocking direction between this portion 30 and the femur, while, considering the fitted encasement of the femur by the surface 12 of the block 10, the portion 30 is jammed in many directions with respect to the specific reliefs of the femur, to which this portion 30 fits.

At the end of this surgical step, the portion 30 may be disengaged and the femur bears the aforementioned secondary pins, it being recalled that the latter are either those which have passed into the holes 37 and 38, as bone preparations tools 63 and 64, and which have been left in place in the femur, or pins which, after disengagement of the portion 30, are added and anchored in blind holes made just before the femur by a boring bit or the like, which acted on the femur through the holes 37 and 38, as a bone preparation tool 63 and 64.

Once the surgeon has disengaged the secondary portion 30 of the block 10 by moving it away from the surface of the femur B, the surgeon continues the surgical operation. The surgeon uses a cutting block or, more generally, any system for preparing the femur, by positioning this block or this system using the aforementioned secondary pins.

As an alternative not shown, the block 10 may be shaped differently, notably for adapting to a bone different from the femur B of FIG. 1. Thus, the secondary portion 30 may not include two branches 31 and 32, or otherwise may include an intermediate portion arranged between the portion 23 and the branches 31 and 32. In this case, the disengagement mechanism 40 may be distributed in a single disengagement region located between this intermediate portion and the portion 23. Such a disengagement region is then shaped in a comparable way with one of the regions 41 and 42 described above, with a single enveloping cavity and vents, the respective profiles of which are adapted to this particular arrangement. Within the extension of the foregoing considerations, it is understood that the presence, within the portion 30, of the branches 31 and 32 described above or more generally the presence of two or more similar branches, more or less individualized, is but one non-limiting example of an embodiment of the present invention.

FIGS. 6 to 28 illustrate various alternatives of mechanical disengagement mechanisms suitable for equipping the instrumentation 1 according to embodiments of the invention.

The instrumentation 1 may include a specific block 10 provided with a mechanism for mechanical disengagement of the secondary portion 30 with respect to the main portion 20. The block 10 and its portions 20 and 30 are partly and schematically illustrated in FIGS. 6 to 28, at the junction area 16. With a purpose of simplification, the portions 20 and 30 are illustrated by parallelepipedal elements aligned relatively to each other, with a single disengagement region between them. The surface 14 is only referenced for illustrating the orientation of the block 10 and of the mechanical disengagement mechanism with respect to the bone B, not shown, while the supporting surface is not referenced. Considering this schematic illustration, it is nevertheless understood that the block 10 is shaped in order to fit the surface of the bone B, as in the example of FIGS. 1 to 5.

Figure 6:
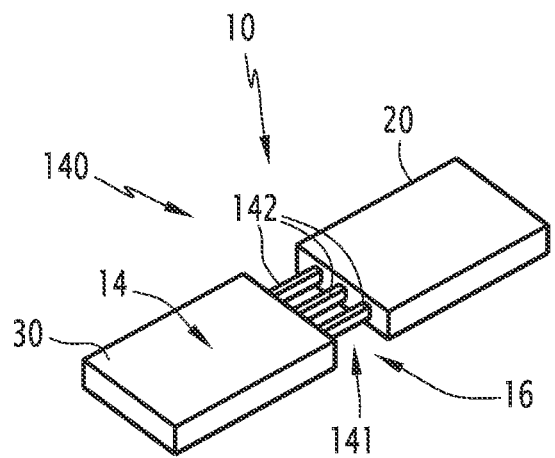
FIG. 6 is a partial perspective view of instrumentation according to another embodiment of the invention.

In FIG. 6 is illustrated the mechanical disengagement mechanism 140 belonging to another embodiment of instrumentation 1. An intermediate space 141 is made between the portions 20 and 30, thereby forming a discontinuity of the surface 14. The mechanism 140 includes bars 142, more specifically three bars 142 in the example of FIG. 6, which extend through the intermediate space 141 and mechanically connect the portions 20 and 30. These bars 142 may easily be destroyed by breaking or tearing away, when sufficient tension is exerted by the surgeon on the secondary portion 30, along a direction for moving them away with respect to the main portion 20. If the material of the bars 142 is rather brittle, the latter break suddenly, while if the material of the bars 142 is rather ductile, the latter will deform by constriction, notably until separation of the portions 20 and 30. Thus, the mechanical disengagement of the portion 30 with respect to the portion 20 and to the bone B is achieved irreversibly by breaking of the bars 142. As an alternative, the mechanism 140 may include a different number of bars 142, or the latter may be shaped differently without departing from the scope of the invention.

Figure 7:
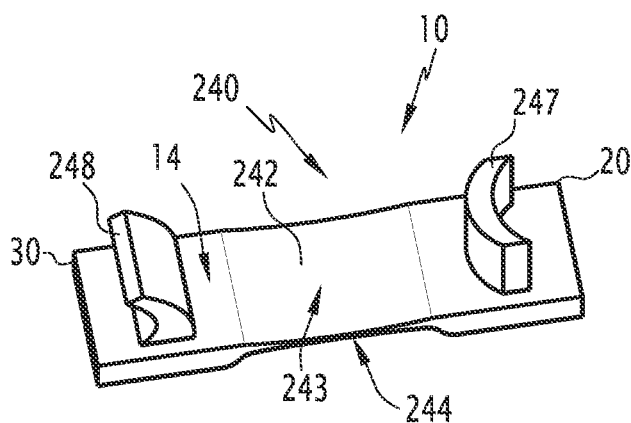
FIG. 7 is a partial perspective view of instrumentation according to another embodiment of the invention.

In FIG. 7 is illustrated mechanical disengagement mechanism 240 belonging to another embodiment of instrumentation 1. The mechanism 240 includes a substantially planar platelet 242 which mechanically connects the portions 20 and 30. The platelet 242 is thinner than the portions 20 and 30, with a first concave cup 243 made on the platelet 242 on the side of the surface 14 and a second concave cup 244 made on the platelet 242 on the side opposite to the surface 14. In the example of FIG. 7 the cup 244 forms a more pronounced material recess than the cup 243. The mechanism 240 also includes handling grips 247, 248 made on the surface 14, on the main portion 20 and on the secondary portion 30 respectively. In the example of FIG. 7, the grip 247 is shaped so as to receive the forefinger of the surgeon, while the grip 248 is shaped in order to receive the thumb of the surgeon. In practice, mechanical disengagement of the portion 30 with respect to the portion 20 and to the bone B is achieved reversibly, simply by folding the platelet 242. As the folding allows reversible disengagement of the portion 30, the surgeon has the possibility of repositioning this secondary portion 30 on the bone B in order to achieve resumption of the borings, if need be. Alternatively, the platelet 242 and the cups 243 and 244, as well as the grips 247 and 248, may be conformed differently without departing from the scope of the invention.

Figure 8:
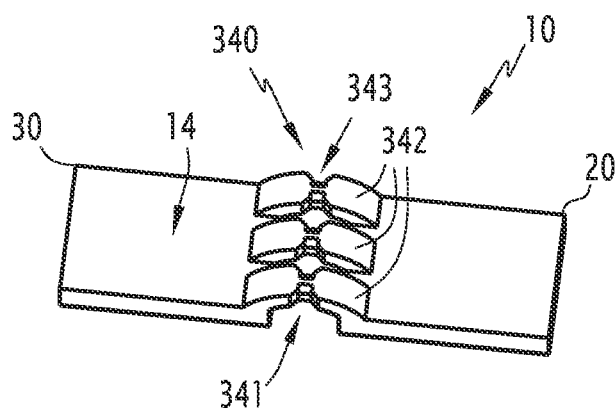
FIG. 8 is a partial perspective view of instrumentation according to another embodiment of the invention.

In FIG. 8 is illustrated mechanical disengagement mechanism 340 belonging to another embodiment of instrumentation 1. An intermediate space 341 is made between the portions 20 and 30, thereby forming a discontinuity of the surface 14. The mechanism 340 includes arches 342, more specifically three arches 342 in the example of FIG. 8, which extend above the intermediate space 341, while being curved upon moving away from the surface 14, and mechanically connect the portions 20 and 30. Each arch 342 includes a thinned portion 343 with respect to the remainder of the arch 342. The thinned portions 343 are located halfway from the portions 20 and 30 and are aligned along a same axis. These arches 342 may easily be destroyed under tension, or in a still more practical way for the surgeon, by being severed using a tool of the cutting pliers type. The irreversible mechanical disengagement of the portion 30 with respect to the portion 20 and to the bone B is therefore achieved by severing the arches 342 at the portions 343. Alternatively the mechanism 340 may include a different number of arches 342, or the latter may be shaped differently, without departing from the scope of the invention.

Figure 9:
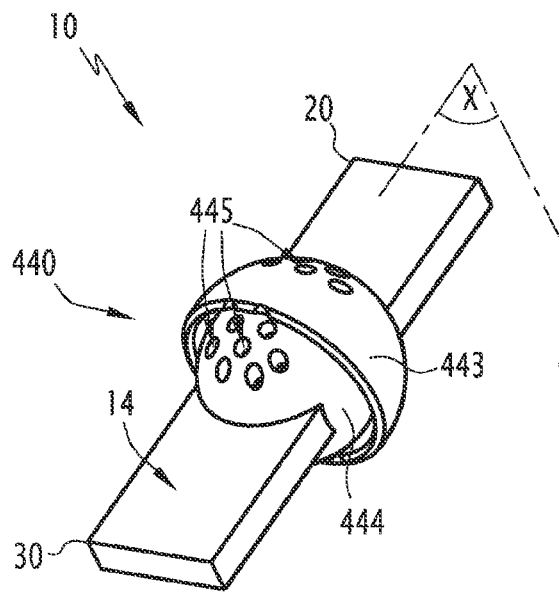
FIG. 9 is a partial perspective view of instrumentation according to another embodiment of the invention.
Figure 10:
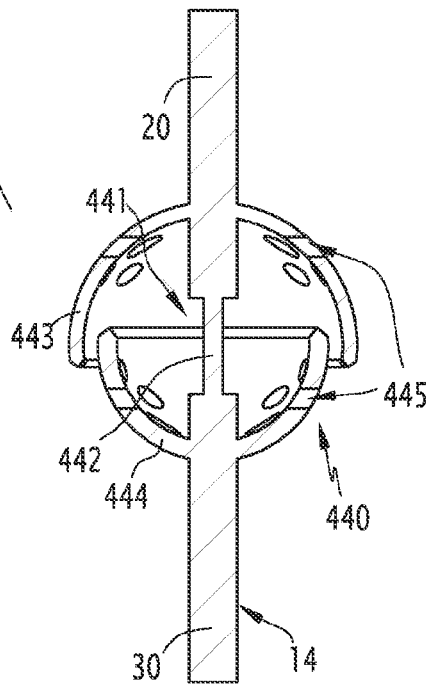
FIG. 10 is a view of a section in the plane X in the FIG. 9.

In FIGS. 9 and 10 is illustrated mechanical disengagement mechanism 440 according to yet another embodiment of instrumentation 1. The mechanism 440 includes a space 441 and bars 442, respectively similar to the space 141 and to the bars 142 of the mechanism 140 described above. The mechanism 440 also includes a first hemispherical dome 443 made on the portion 20 and a second hemispherical dome 444 made on the portion 20. The dome 443 has a greater diameter than the diameter of the dome 444, so that the dome 444 is partly housed inside the dome 443, without any contact between them. Together, the two domes 443 and 444 surround the space 441 and the bars 442. Further, a plurality of through-orifices 445 are made in each of the domes 443 and 444. These domes are provided for recovering possible debris in the case of brittle failure of the bars 442. Indeed, such debris would risk being introduced into the body of the patient, something which must absolutely be avoided in surgery. The orifices 445, as well as the distance between the domes 443 and 444, are dimensioned so as to avoid that such debris escape, while allowing blowing off of the powder contained in the domes 443 and 444 after making the block 10 and the mechanism 40 by sintering. During the failure of the bars 442, the domes 443 and 444 are pivotally connected and the dome 444 may then be disengaged out of the dome 443, while ensuring that possible debris are evacuated.

In this embodiment, it is understood that the portions 20 and 30 are provided, at the junction area 16, with additional material portions giving the possibility of separating the mechanism 440 with respect to the supporting surface of the block 10 and to the bone B. Indeed, the presence of the domes 443 and 444 prevent positioning of the mechanism 440 in proximity to the bone B, according to embodiments of the present invention.

Figure 11:
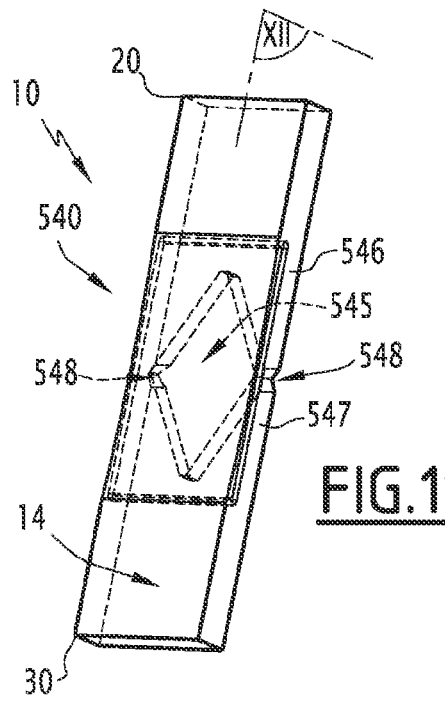
FIG. 11 is a partial perspective view of instrumentation according to another embodiment of the invention, certain elements being shown in transparence and illustrated by dashed lines.
Figure 12:
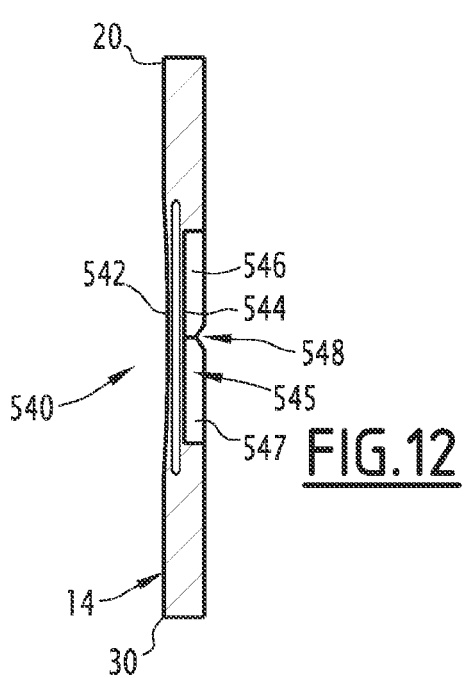
FIG. 12 is a sectional view in the median plane XII in FIG. 11.

In FIGS. 11 and 12 is illustrated mechanical disengagement mechanism 540 according to yet another embodiment of instrumentation 1. The mechanism 540 includes a foldable platelet 542 comparable to the platelet 242 described above, as well as a destructible platelet 544. The mechanism 540 also includes a rhombus-shaped cavity 545, opening opposite to the face 14 and closed at the platelet 544. The rhombus-shaped cavity 545 has two apices respectively directed towards the portions 20 and 30, as well as two apices each including a localized weakening area 548 of the material between a portion 546 secured to the portion 20 and a portion 547 secured to the portion 30. When the surgeon handles the portion 30 according to a folding action on the platelet 542, in a comparable way with the folding of the platelet 242, the areas 548 then fail and their failure, propagating towards the surface 14, causes tearing of the platelet 544 and separation of the portions 546 and 547. Thus, the mechanical disengagement of the portion 30 with respect to the portion 20 and to the bone B is achieved by combining folding and failure. This disengagement is reversible via the platelet 542. Alternatively, the mechanism 540 combining folding and failure may be differently shaped without departing from the scope of the invention.

In FIGS. 13 and 15 is illustrated mechanical disengagement mechanism 640 according to yet another embodiment of instrumentation 1. The mechanism 640 includes a tongue 642 and a portion 644 separated by an intermediate space 641. The tongue 642 is located on the side opposite to the surface 14 and connected to the portion 20, but not to the portion 30. The portion 644 is located on the side of the surface 14 and connected both to the portion 20 and to the portion 30. The thickness of the portion 644, measured in a direction normal to the surface 14, may be larger than the thickness of the tongue 642. The portion 644 includes a cavity 645 for receiving a tool, not shown, for mechanical disengagement of the portion 30. This cavity 645 opens into the space 641 and at the surface 14. On either side of the cavity 645, the portion 644 includes filamentary elements 646 connecting the side connected to the portion 20 to the side connected to the portion 30. The tongue 642 includes, facing the cavity 645 along the direction normal to the surface 14, a housing 643 for supporting the tool introduced through the cavity 645. Such tool may be of the retractor type, initially having a shape suitable for penetrating into the cavity 645.

In practice, in a first phase, the tool is introduced into the cavity 645 and then will abut against the tongue 642, in the housing 643. In a second phase, the tool is deployed in the cavity 645 so as to exert opposite forces on the element 646, until their tearing causes irreversible separation of the portions 20 and 30. The mechanism 640, in particular the elements 646, may be shaped differently without departing from the scope of the invention, by forming a material link between the portions 20 and 30, while being easily destructible under the action of the tool introduced into the cavity 645. The presence of the tongue 642 avoids scraping of the tool against the bone B. The housing 643 is optional, but facilitates the positioning of the tool inside the mechanism 640.

Figure 16:
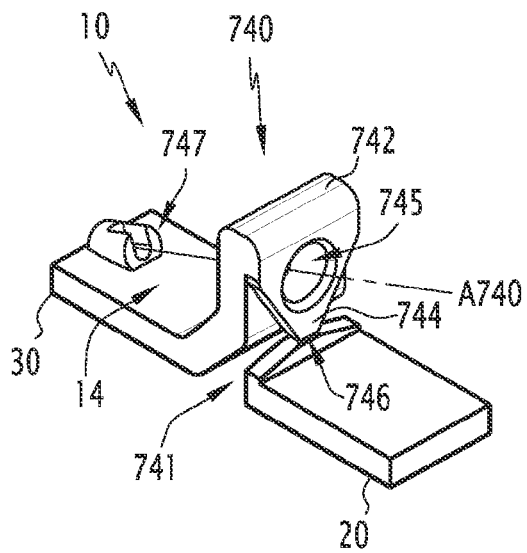
FIG. 16 is a partial perspective view of instrumentation according to another embodiment of the invention.

In FIG. 16 is illustrated mechanical disengagement mechanism 740 according to another embodiment of instrumentation 1. An intermediate space 741 is made between the portions 20 and 30. The mechanism 740 includes a member 742 which extends, protruding from the surface 14, above the space 741. The member 742 includes a tongue 744 attached to the portion 20 through a thinned portion 746, which thus forms a localized weakening area of the material. The member 742 is crossed by an orifice 745 centered on an axis A740 and provided for receiving a tool, for example of the screwdriver type. A guiding element 747 may be made on the surface 14 of the portion 30, in the extension of the axis A740, in order to receive the tip of the tool. In practice, the tool is introduced into the orifice 745 along the axis A740 in a first phase, and is then lifted up by bearing upon the element 747 and by exerting forces opposite to the surface 14 inside the orifice 745 in a second phase, until the irreversible mechanical disengagement of the portion 30 occurs by failure of the portion 746 in a third phase. Alternatively, the member 742, the orifice 745 and the portion 746 may be shaped differently without departing from the scope of the invention. For example the thinned portion 746 may connect the member 742 to the portion 30, or else the member 746 may include two thinned portions connecting it to each of the portions 20 and 30. According to another example, the orifice 745 may have a shape different from the example of FIG. 16, for example a square shape allowing failure of the portion 746 by rotation of the tool in the orifice 745.

Figure 17:
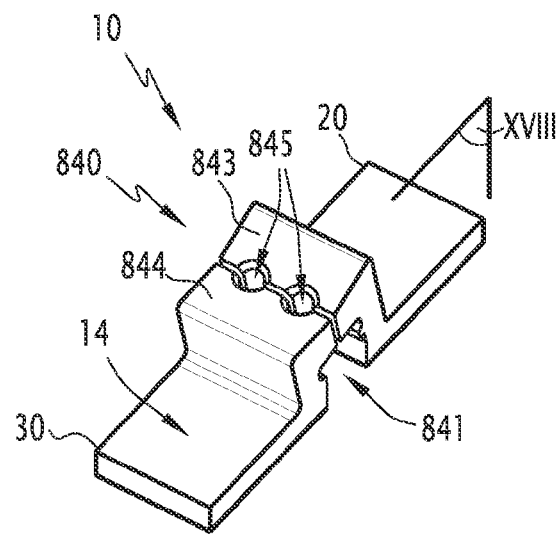
FIG. 17 is a partial perspective view of instrumentation according to another embodiment of the invention.
Figure 18:
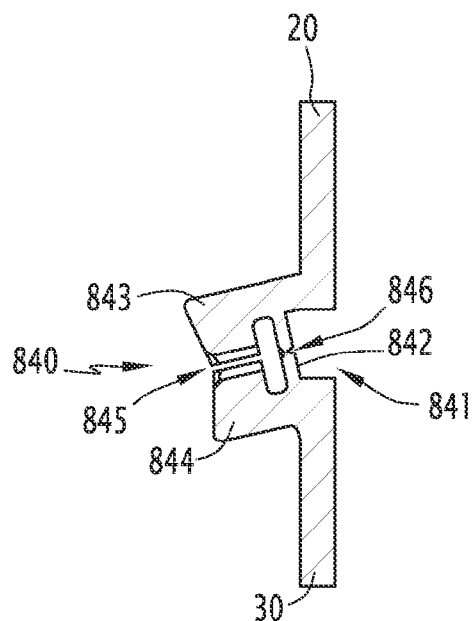
FIG. 18 is a sectional view in the median plane XVIII in FIG. 17.

In FIGS. 17 and 18 is illustrated mechanical disengagement mechanism 840 according to yet another embodiment of instrumentation 1. An intermediate space 841 is made between the portions 20 and 30. The mechanism 840 includes a platelet 842 which connects a first element 843 secured to the portion 20 with a second element 844 secured to the portion 30. The elements 843 and 844 are formed, protruding beyond the surface 14, while the platelet 842 extends above the space 841. The platelet 842 includes a thinned portion 846, thereby forming a localized weakening area of the material. Two holes 845 are made between the elements 843 and 844, facing the portion 846. The holes 845 are provided for introducing and positioning a tool, which may bear against the portion 846 until it breaks. Alternatively, the means 840 may be shaped differently without departing from the scope of the invention, for example with a number of holes 845 which depends on the width of the block 10 at the junction area 16.

In the examples of FIGS. 1 to 18, the mechanical disengagement mechanisms 40 to 840 may be made with both of the portions 20 and 30 of the block 10 formed of the same material, according to embodiments of the present invention.

Figure 19:
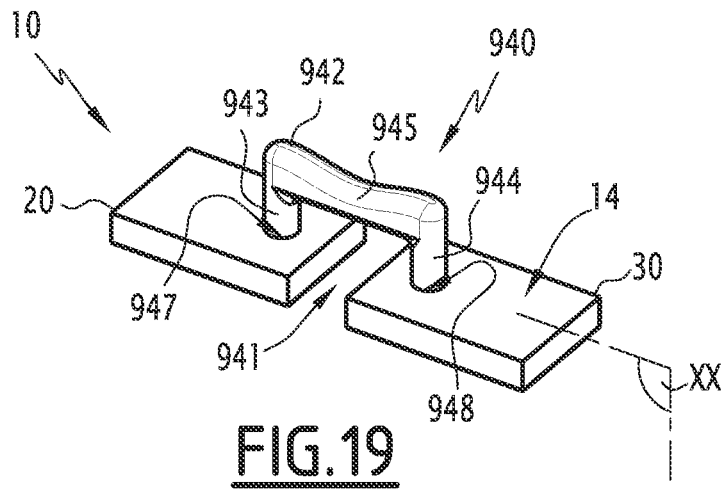
FIG. 19 is a partial perspective view of instrumentation according to another embodiment of the invention.
Figure 20:
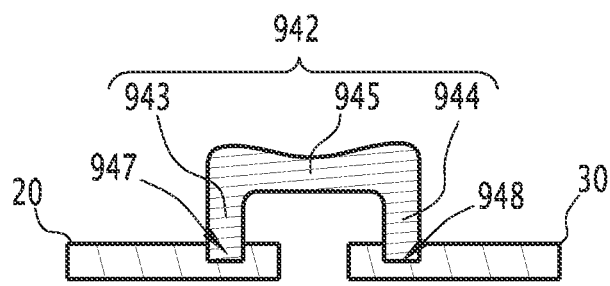
FIG. 20 is a sectional view in the median plane XX in FIG. 19.

FIGS. 19 and 20 illustrate mechanical disengagement mechanism 940 according to yet another embodiment of instrumentation 1. An intermediate space 941 is made between the portions 20 and 30. The mechanism 940 includes a member 942 with the shape of bridge or of a U, with two tabs 943 and 944 being connected through a central portion 945. Orifices 947 and 948 are respectively made in the portions 20 and 30, while opening at the surface 14. In practice, the member 942 is secured to the portions 20 and 30 during a pre-operative phase with the tab 943 which is fastened with clips in the orifice 947, the tab 944 which is fastened with clips in the orifice 948, while the portion 945 extends above the space 941. During a per-operative phase, the member 942 is removable from the specific block 10 by unclipping the tabs 943 and 944. In other words, the connection between the member 942 and the portions 20 and 30 is temporary, and the mechanical disengagement of the portions 30 is reversible. Thus, this portion 30 may be easily repositioned on the bone if need be.

Figure 21:
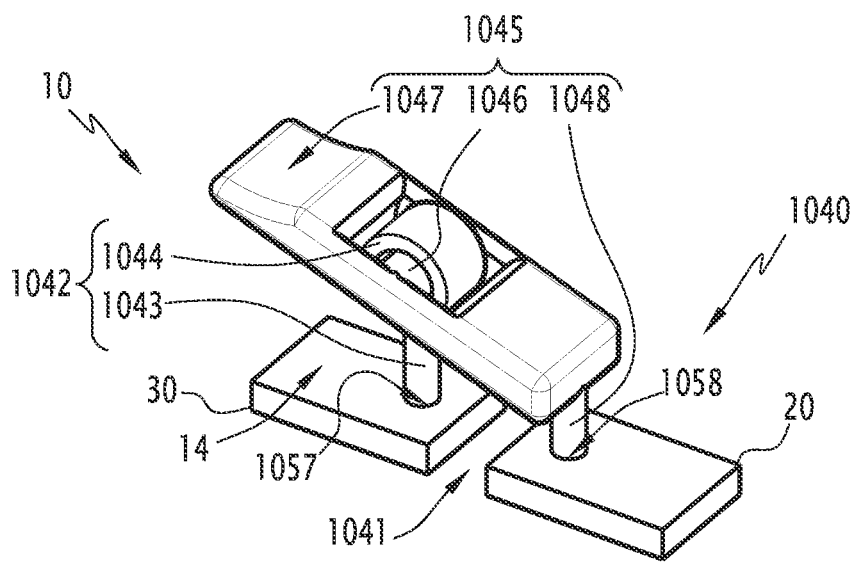
FIG. 21 is a partial perspective view of instrumentation according to another embodiment of the invention.

FIG. 21 illustrates mechanical disengagement mechanism 1040 according to yet another embodiment of instrumentation 1. An intermediate space 1041 is made between the portions 20 and 30, the mechanism 1040 includes a member 1042 provided with a rod 1043 secured to the portion 30 and with a bearing 1044 positioned at the end of the rod 1043 opposite to the portion 30. The rod 1043 may be screwed or clipped into an orifice 1057 made in the portion 30, at the surface 14. Alternatively, the rod 1043 is made with the portion 30 in the same material. The mechanism 1040 also includes a member 1045 with a globally parallelepipedal shape, provided with a central portion 1046 in a pivotal connection in the bearing 1044, with a first supporting end 1047 and a second end, opposite to the end 1047 with respect to the central portion 1046, including a rod 1048 which extends toward the surface 14 of the portion 20. An orifice 1058 is made in the portion 20, at the surface 14. The mechanism 1040 is secured to the portions 20 and 30 during a pre-operative phase, with the rod 1048 which is fastened with clips in the orifice 1058 and the member 1045 which extends above the space 1041. During a per-operative phase, pressing on the end 1047, through a lever effect, pivots the member 1045 in the bearing 1044 and unclips the rod 1048 from the orifice 1058. In other words, the connection between the mechanism 1040 and the portions 20 and 30 is temporary, and the reversible mechanical disengagement of the portion 30 may be carried out by simple unclipping. Thus, this portion 30 may be easily repositioned on the bone if need be.

In FIGS. 19 to 21, the mechanisms 940 and 1040 may be partly made in an elastic material. As a non limiting example, the elements 942, 1043 and 1048 may be made in an elastic material. Such an elastic material contributes to the tensioning of the main portion and of the secondary portion on the one hand and guarantees the mechanical strength of the assembly during the positioning of the block, as well as during boring on the other hand.

Figure 22:
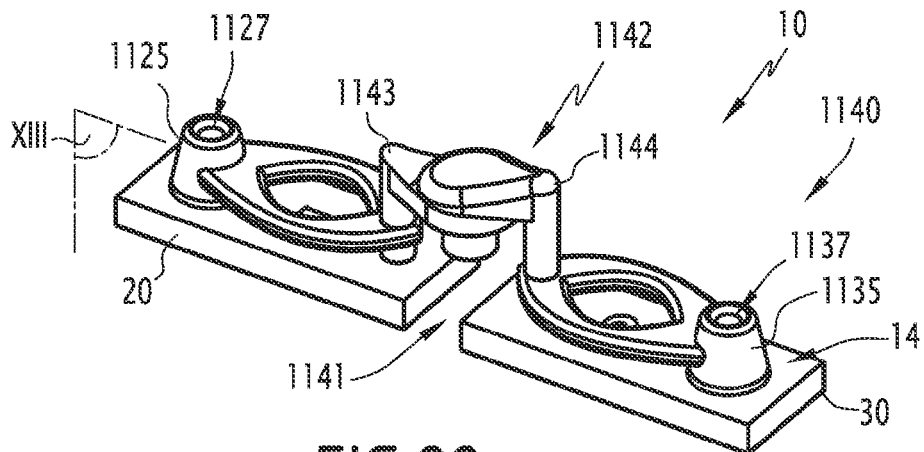
FIG. 22 is a partial perspective view of instrumentation according to another embodiment of the invention.
Figure 23:
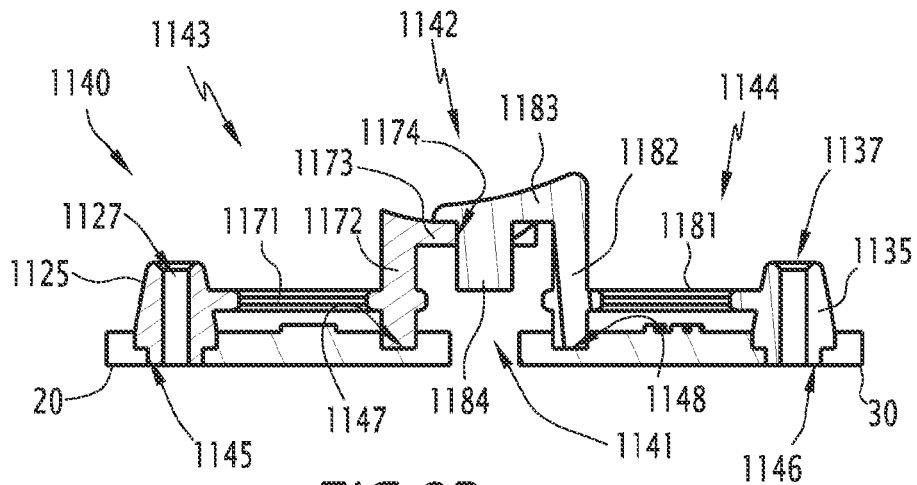
FIG. 23 is a sectional view including the median plane XXIII in FIG. 22.

FIGS. 22 and 23 illustrate mechanical disengagement mechanism 1140 according to yet another embodiment of instrumentation 1. An intermediate space 1141 is made between the portions 20 and 30. The mechanism 1140 includes a first connecting member 1143 and a second connecting member 1144 suitable for forming a mechanical link 1142 of the bridge type between the portions 20 and 30, above the space 1141. The member 1143 includes a stud 1125 provided with a through-hole 1127, with two branches 1171 connecting the stud 1125 to a tab 1172, with a portion 1173 positioned at one end of the tab 1172 opposite to the branches 1171 and with an orifice 1174 made on the portion 1173. The member 1144 includes a stud 1135 provided with a through-hole 1137, with two branches 1181 connecting the stud 1135 to a tab 1182, with a portion 1183 positioned at one end of the tab 1182 opposite to the branches 1181 and with a pin 1184 made on the portion 1183 parallel to the tab 1182. Orifices 1145 and 1147 are made in the portion 20, while orifices 1146 and 1148 are made in the portion 30, opening at the surface 14. The studs 1125 and 1135 and the holes 1127 and 1137 are respectively comparable to the studs 25 and 35 described above, in other words, are shaped for guiding a tool or pins. The tabs 1172 and 1182 are comparable to the tabs 943 and 944 as described above. The branches 1171 and 1181 are shaped for following the profile of the surface 14 between the studs and the tabs. The portions 1173 and 1183 are shaped so as to bear against each other, with the pin 1184 which will be housed in the orifice 1174, thereby forming the link 1142. The constitutive elements of the members 1143 and 1144 may be shaped differently without departing from the scope of the invention.

In practice, the mechanism 1140 is secured to the portions 20 and 30 during a pre-operative phase, with the elements, 1125, 1135, 1172 and 1182 which are respectively clipped in the orifices 1145, 1146, 1147 and 1148, while the link 1142 is formed above the space 1141. More specifically, the member 1143 is attached to the portion 20, and then the member 1144 is attached to the portion 30 and to the member 1143. Preferably, by applying metal boring guns, it is possible to make the whole of the orifices 1145, 1146, 1147 and 1148 with great accuracy. During a per-operative phase, after attaching the pins 61 and 62 in the bone B through the specific block 10, the member 1144 is removable from the specific block 10 by unclipping the stud 1135, the tab 1148 and the nipple 1184. In other words, reversible mechanical disengagement of the portion 30 may be achieved by simply unclipping the member 1144. For its part, the unclipping of the member 1143 may be unnecessary due to the presence of the stud 1125 provided with the orifice 1127.

When operating, the studs 1125 and 1135 are used for guiding a tool in order to pierce the bone B. In other words, the guiding studs 1125 and 1135 are directly borne by the mechanical disengagement mechanism 1140. The connecting members 1143 and 1144 may be made of metal. When boring is carried out in the holes 1127 or 1137 through the studs 1125 or 1135, the risk of forming debris or chips is reduced or eliminated when the members 1143 and 1144 are formed of metal. The studs 1125 and 1135 and the orifices 1127 and 1137 are configured with a specific direction and cutting height, depending on the pre-operative plan specific to each patient.

As an alternative not shown of the mechanism 1140, the studs 1125 and 1135 may include mechanisms for translational or rotational displacement for adjusting their position and tilt relatively to the specific block 10.

Figure 24:
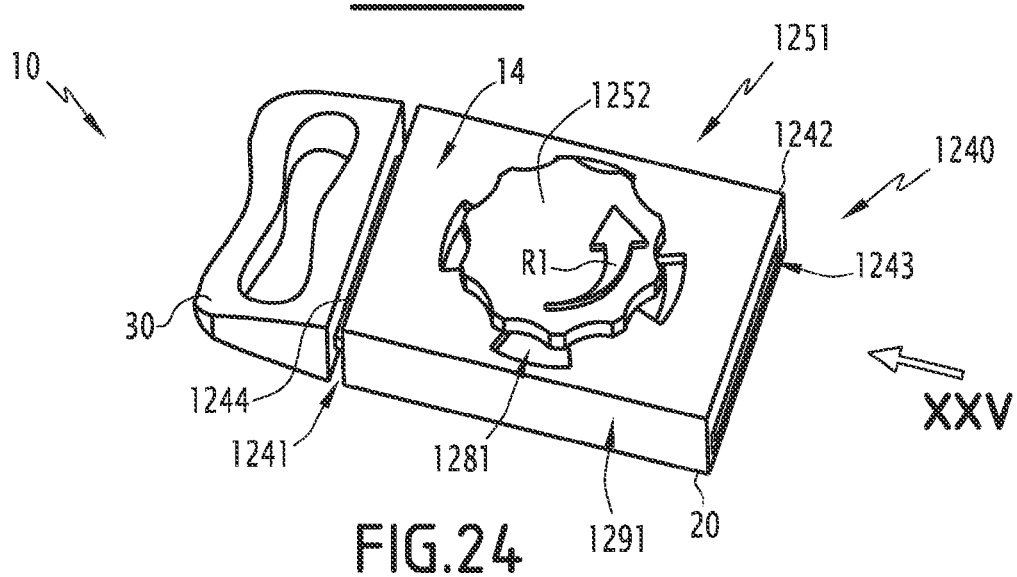
FIG. 24 is a partial perspective view of instrumentation according to another embodiment of the invention.
Figure 25:
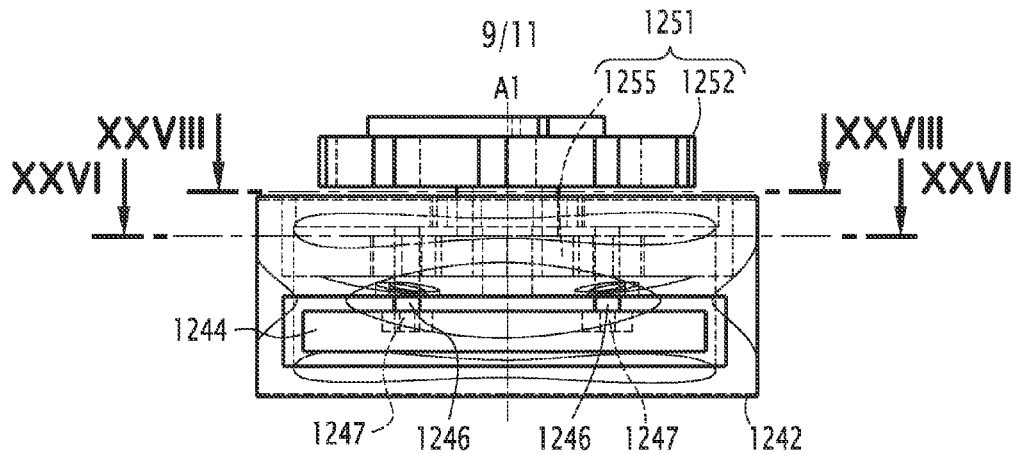
FIG. 25 is an elevational view along the arrow XXV in FIG. 24, certain elements being shown in transparence and illustrated by dashed lines.
Figure 26:
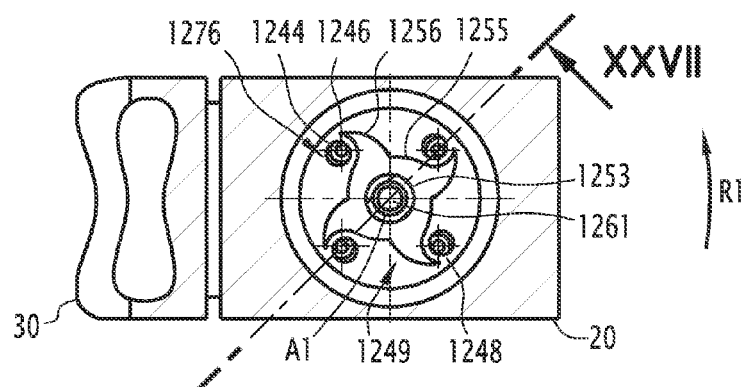
FIG. 26 is a sectional view in the plane XXVI in FIG. 25.
Figure 27:
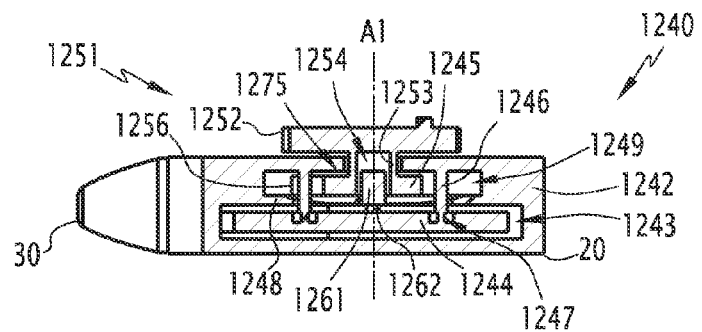
FIG. 27 is a sectional view in the plane XXVII in FIG. 26.

FIGS. 24 and 28 illustrate mechanical disengagement mechanism 1240 according to yet another embodiment of instrumentation 1. An intermediate space 1241 is made between the portions 20 and 30. The mechanism 1240 includes a box 1242 provided with a drawer compartment 1243 in which a tongue 1244 may slide. The box 1242 is secured to the portion 20. The tongue 1244 is secured to the portion 30 and initially connected to a wall 1245 of the box 1242 via elongated pins 1246. Thinned portions 1247 of the pins 1246 connect these pins 1246 with the tongue 1244. An intermediate wall 1248 separates the compartment 1243 from a compartment 1249, which is arranged between the wall 1245 and the wall 1248. The pins 1246 extend through orifices 1276 made through the wall 1248.

The mechanism 1240 also includes a rotary member 1251 centered on axis A1 and partly extending outside the box 1242. More specifically, the member 1251 includes a manipulation head 1252 located outside the box 1242 on the side of the surface 14, a propeller 1255 which is located in the compartment 1249, as well as a portion 1253 which connects the head 1252 and the propeller 1255 and extends along the axis A1 through an aperture 1275 made in the wall 1245 of the box 1242. The propeller 1255 includes blades 1256 radially distributed around the axis A1. The portion 1253 includes a cylindrical recess 1254 centered on the axis A1, opening at the propeller 1255 and not opening at the head 1252. A cylindrical pin 1261 extends from the tongue 1254 along the axis A1 towards the head 1252, is attached to the tongue 1244 by a thinned portion 1262 and is received into the cylindrical recess 1254. Thus, the pin 1261 and the portion 1253 are in a pivot connection around the axis A1. In other words, the pin 1261 is suitable for supporting the member 1251 pivoting according to a rotary movement R1 around the axis A1.

In practice, the surgeon pivots the member 1251 around the axis A1 according to rotation R1, by manipulating the head 1252. The member 1251 then pivots around the pin 1261. The blades 1256 of the propeller 1255 will come into contact with the pins 1256 and exert forces on these pins 1256 until they fail, notably at the thinned portions 1247. Thus, the tongue 1244 is detached from the pins 1256 and therefore from the box 1242, and may slide in the compartment 1243. At this stage, the pin 1261 is detached from the tongue 1244 at the thinned portion 1262, subject to shearing between the portion 1253 and the tongue 1244. In other words, the mechanical disengagement of the portions 30 secured to the tongue 1244 is achieved by failure of the pins 1256 during the rotation of the propeller 1255, and then by sliding of the tongue 1244.

Preferably, the mechanical disengagement mechanism 1240 is made both with the main portion 20 and the secondary portion 30 formed of the same material. In the case when the mechanism 1240, which has complex shapes, is made by powder sintering, then the residual powder present in the box 1242 may be removed during the pre-operative phase. For this purpose, the box 1242 is provided with orifices 1281 made through its wall 1245, as shown in FIGS. 24 and 28. Additionally the box 1242 may also include orifices for discharging powder made through side walls 1291. However, the box 1242 does not include any orifices on its wall opposite to the wall 1245 and to the surface 14. Indeed, during the failure of the pins 1256, the possible debris is recovered in the box 1242. If the box included orifices made through its wall opposite to the surface 14, the debris would be able to escape on the side of the bone B of the patient, which may be avoided.

In the non-limiting example of FIGS. 24 to 28, the pins 1246, the blades 1256 and the apertures 1276 are four in number. Alternatively, the mechanism 1240 may be shaped differently without departing from the scope of the invention. For example the elements 12466, 1256 and 1276 may have a different number of them. According to another example, the mechanism 1240 may not include any pin 1261.

FIGS. 29 to 34 illustrate instrumentation 1' according to yet another embodiment of the present invention. The bone B is schematized as a sphere and is covered with bone cartilage C. In particular, the observation direction of FIG. 30 corresponds to the latero-medial direction of a femur, while the antero-posterior direction is illustrated by an arrow D1. The instrumentation 1' includes a specific block 10', as well as mechanical disengagement mechanism 40' made on the specific block 10'. The other constitutive elements of the instrumentation 1' have similar operation, but a different structure, as prepared with the constitutive elements of the instrumentation 1 of FIGS. 1 to 5. With a purpose of simplification, these constitutive elements 12, 14, 16, 20, 27, 28, 30, 37 and 38 include the same numerical references as those of instrumentation 1. The instrumentation 1' also includes bone anchoring pins, with only pin 63 being illustrated in FIG. 32.

Figure 32:
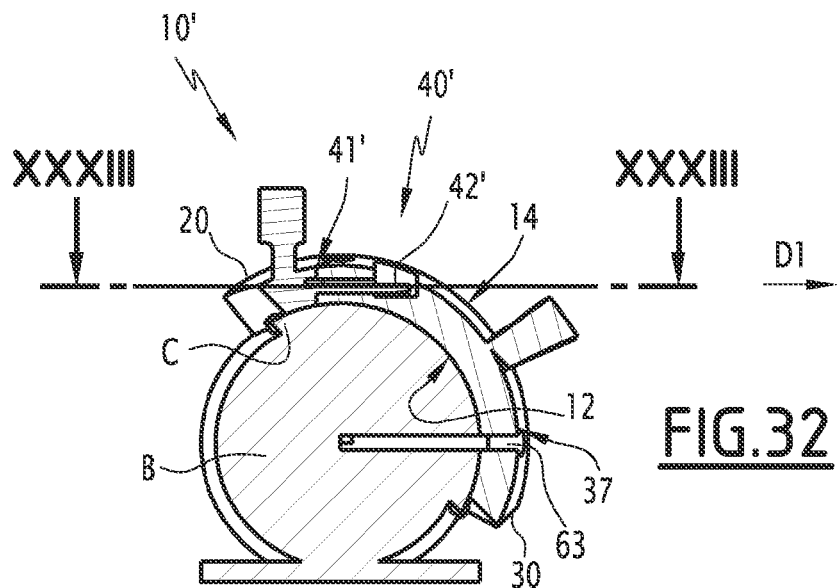
FIG. 32 is a sectional view along the line XXXII-XXXII in FIG. 31.
Figure 33:
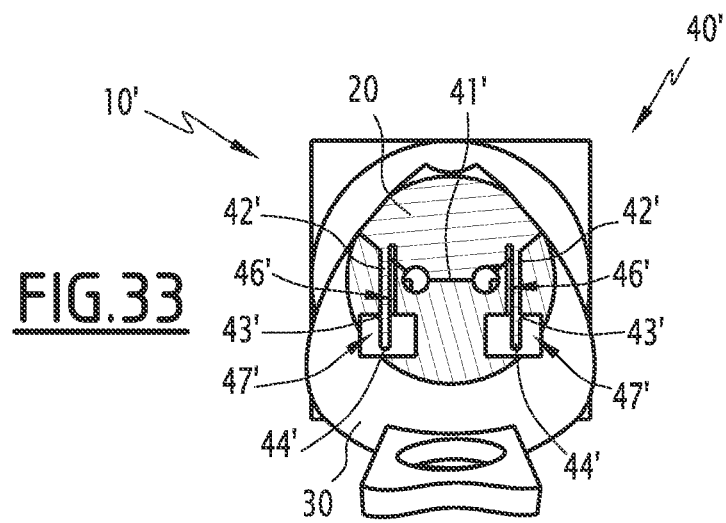
FIG. 33 is a sectional view along the line XXXIII-XXXIII in FIG. 32.
Figure 34:
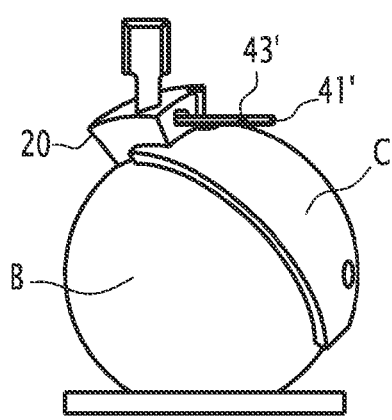
FIG. 34 is a view similar to FIG. 30, the instrumentation being partly shown.

The block 10' of instrumentation 1' includes a main portion 20 and a secondary portion 30, both entirely detachable from the bone B. The block 10' is specially designed so as to fit the profile of the cartilage C, which has irregularities, as shown in FIGS. 30, 32 and 34. The block 10' therefore is not fitted onto the bone B and removed from this bone B in the same way as block 10 of instrumentation 1.

Under these conditions, the portions 20 and 30 are disconnected. The junction area 16 between the portions 20 and 30 is delimited at the holes 27 and 28 for letting through pins. The manufacturing of the portions 20 and 30 is carried out separately, and these portions 20 and 30 are then assembled by fastening with clips, due to the mechanism 40'. Alternatively, both portions 20 and 30 are manufactured together and then detached afterwards. In order to facilitate their handling, the portions 20 and 30 respectively include a handle 29 and a handle 39. The portion 20 is positioned on the bone B and the cartilage C along the antero-posterior direction D1, while the portion 30 is positioned according to the postero-anterior direction opposite to the direction D1.

More specifically, the mechanism 40' includes a separation 41' which extends according to a broken plane in the junction area 16 and passes through the orifices 27 and 28. The portions 20 and 30 are adapted so as to be supported at the separation 41'. The mechanism 40' also includes two rods 42' which extend from the portion 20 along the antero-posterior direction D1, as well as two cavities 46' which are made in the portion 20 and are provided so as to receive the rods 42' along the direction D1. The cavities 46' open at the separation 21' on the one hand and into apertures 47' made at the surface 14 in the portion 30, on the other hand. Protrusions 43' are formed on the rods 42', on the side of the ends 44' of the rods 42' opposite to the portion 20, protruding along a direction perpendicular to the direction D1. The rods 42' are elastically deformable and tend to move away from each other.

When the portions 20 and 30 are assembled in order to form the block 10', the rods 42' penetrate into the cavities 46', the ends 44' are positioned in the apertures 47', while the protrusions 43' are blocked against the walls of these apertures 47', thereby forming a connection by the clipping of the rods 42' in the portions 30. By having the surgeon press his/her fingers onto the ends 44', by bringing both ends 44' closer, it is possible to unclip the portions 20 and 30. In other words, the mechanism 40' equipping the instrumentation 1' forms both a mechanism for mechanical engagement and disengagement of the portions 20 and 30 with each other and also with the bone B. In particular, the rods 42' and the protrusions 43' form elements for having the portion 20 temporarily adhere to the portion 30.

The mechanical disengagement mechanisms 40 to 1240 and 40' may be shaped differently without departing from the scope of the invention.

The disengagement mechanisms include at least one patient-specific cavity, according to embodiments of the present invention. For example, two cavities may be made on the block, according to a patient-specific geometry. The cavities may be associated with elements promoting sectility and retention of debris. When the block is made by powder sintering, each cavity may include at least one aperture opening outside the block, on at least one face of this block. Each cavity may be provided according to a geometry allowing satisfactory mechanical strength to be maintained along the bearing direction of the block towards the bone. Each cavity may follow a trajectory corresponding to a particular sectility or folding path, along which the mechanical strength of the disengagement mechanism is minimum for example in proximity to the boring studs.

Further, the technical features of the various embodiments of the present invention may either in totality or selectively, be combined together. Thus, the instrumentation and the mechanical disengagement mechanism may be adapted in terms of simplicity of manufacturing and of use, of cost and performance. In particular the mechanical disengagement mechanism may be reversible or irreversible and adapted to the preferences of the surgeon. Further, the mechanical disengagement mechanism may be adapted for preparing a given bone of the patient.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. Surgical instrumentation specific to a patient (1; 1') for preparing a bone (B) of the patient, the instrumentation comprising a patient-specific block (10; 10') delimiting a fixed supporting surface (12) on the bone (B), which is shaped so as to be specifically fitted to this bone (B), and including a main portion (20) which partly delimits the fixed supporting surface (12) and which delimits at least two primary orifices (27, 28) for respectively letting through a primary pin (61, 62), these primary orifices passing through the block (10; 10') between the supporting surface and an opposite surface (14) of the block, the instrumentation (1; 1') further comprising:
  a secondary portion (30) which belongs to the block (10; 10'), which partly delimits the supporting surface (12) and which includes at least two secondary orifices (37, 38) for respectively letting through a bone preparation tool (63, 64), such as a boring bit or an anchoring pin, these secondary orifices crossing the block between the supporting surface and the opposite surface (14) of the block, and
  means (40; 140; 240; 340; 440; 540; 640; 740; 840; 940; 1040; 1140; 1240; 40') for mechanically disengaging the secondary portion (30) with respect to the main portion (20), suitable for, while the main portion is attached onto the bone (B) by primary pins (61, 62) having passed into the primary orifices (27, 28), making the secondary portion (30) removable with respect to the main portion,
  wherein the mechanical disengagement means (40) comprise at least one patient-specific cavity (43, 44), which extends through the block (10) between the main portion (20) and the secondary portion (30), along a geometrical envelope of the fixed supporting surface (12).

2. The instrumentation (1; 1') according to claim 1, wherein the block (10) and the specific cavity (43, 44) each have a substantially constant thickness (e10; e43, e44), along a direction normal to the fixed supporting surface (12), at the mechanical disengagement means (40).

3. The instrumentation (1) according to claim 1, wherein the block (10) includes at least one vent (45; 46) opening into the specific cavity (43; 44) on the one hand and at the fixed supporting surface (12) or the opposite surface (14) of the block (10) on the other hand.

4. The instrumentation (1) according to claim 1, wherein the mechanical disengagement means (40) comprise two cavities (43, 44) specific to this patient, which extend through the block (10) along a geometrical envelope of the fixed supporting surface (12).

5. The instrumentation (1) according to claim 1, wherein said or each specific cavity (43, 44) includes at least one aperture opening outside the block (10).

6. The instrumentation (1) according to claim 1, wherein the mechanical disengagement means (40; 140; 240; 340; 440; 540; 640; 740; 840; 940; 1040; 1140; 1240; 40') are further suitable for, while the secondary pins (63, 64) are passed into the secondary orifices (37, 38), making the secondary portion (30) removable with respect to the main portion (20) by sliding along the secondary pins.

7. The instrumentation (1) according to claim 1, wherein the mechanical disengagement means (40; 140; 240; 340; 440; 540; 640; 740; 840; 940; 1040; 1140; 1240;) are made both with the main portion and the secondary portion in the same material.

8. The instrumentation (1) according to claim 1, wherein the mechanical disengagement means (40; 140; 240; 340; 440; 540; 640; 740; 840; 940; 1040; 1140; 1240;) are made both with the main portion and the secondary portion in the same material during the manufacturing of the block (10) by laser powder sintering.

9. The instrumentation (1) according claim 1, wherein the mechanical disengagement means (40; 140; 240; 340; 440; 540; 640; 740; 840; 940; 1040; 1140; 1240;) comprise at least one connecting element (41, 42; 142; 343, 343; 442; 544, 548; 646; 746; 842, 846; 1246, 1247) which connects the main portion (20) and the secondary portion (30) and which may be destroyed by breakage, tearing off and/or by severance.

10. The instrumentation (1) according to claim 9, wherein the mechanical disengagement means (40; 640; 740; 840) comprise at least one aperture (45, 46; 643, 645; 745; 845) for receiving a tool in contact with the connecting element(s) (41, 42; 646; 746; 842, 846) for breaking, tearing off and/or severing the connecting element(s).

11. The instrumentation (1) according to claim 1, wherein the mechanical disengagement means (240; 540) comprise an elastically deformable element (242; 542) which connects the main portion (20) and the secondary portion (30) and allows reversible disengagement by folding the secondary portion (30) with respect to the main portion (20).

12. The instrumentation (1) according to claim 9, wherein the mechanical disengagement means (1240) comprise a rotary member (1251) and in that a rotation (R1) of the rotary member (1251) exerts forces on the connecting element(s) (1246, 1257) for tearing off and/or severing the connecting element(s).

13. The instrumentation (1) according to claim 1, wherein the mechanical disengagement means (940; 1040) are adapted so as to be successively secured to the block (10) and then at least partly detached from the block (10), notably by clipping/unclipping or by screwing/unscrewing.

14. The instrumentation (1') according to claim 1, wherein the mechanical disengagement means (40') are at least partly made with a first portion from among the main portion (20) and a secondary portion (30), in the same material.

15. The instrumentation (1') according to claim 14, wherein the mechanical disengagement means (40') include at least one element (42', 43') for having the first portion temporarily adhere onto a second portion from among the main portion (20) and the secondary portion (30).

* * * * *

UNITED STATES PATENT AND TRADEMARK OFFICE
CERTIFICATE OF CORRECTION

| | |
|---|---|
| PATENT NO. | : 8,920,428 B2 |
| APPLICATION NO. | : 13/677976 |
| DATED | : December 30, 2014 |
| INVENTOR(S) | : Toufik Zakaria and Emmanuel Lizee |

Page 1 of 1

It is certified that error appears in the above-identified patent and that said Letters Patent is hereby corrected as shown below:

Specification

At Column 13, Line 22, change "non limiting" to --non-limiting--.

Claims

At Column 18, Line 15, In Claim 9, after "according" insert --to--.

At Column 18, Line 18, In Claim 9, change "343,343;" to --343;--.

Signed and Sealed this
Eighth Day of December, 2015

Michelle K. Lee
*Director of the United States Patent and Trademark Office*